United States Patent [19]
Markoll

[11] Patent Number: 5,387,176
[45] Date of Patent: * Feb. 7, 1995

[54] TREATMENT OF ACUTE DISEASES AS CAUSED BY THE SPORTS-TYPE INJURIES OF THE MUSCULOSKELETAL SYSTEM EXCLUDING FRACTURES WITH MAGNETIC FIELD THERAPY

[75] Inventor: Richard Markoll, Middlebury, Conn.

[73] Assignee: Bio-Magnetic Therapy Systems Inc., Danbury, Conn.

[*] Notice: The portion of the term of this patent subsequent to Jul. 21, 2009 has been disclaimed.

[21] Appl. No.: 867,362

[22] Filed: Apr. 13, 1992

Related U.S. Application Data

[63] Continuation-in-part of Ser. No. 519,410, May 4, 1990, Pat. No. 5,131,904.

[51] Int. Cl.$^6$ .............................................. A61N 1/00
[52] U.S. Cl. ................................................... 600/14
[58] Field of Search ..................................... 600/9–15

[56] References Cited

U.S. PATENT DOCUMENTS 5,131,904  7/1992  Markoll ............................... 600/14

Primary Examiner—Lee S. Cohen
Assistant Examiner—John P. Lacyk
Attorney, Agent, or Firm—Dallett Hoopes

[57] ABSTRACT

Process involves treating acute diseases of a body organ of the musculoskeletal system by applying a magnetic field by means of an annular coil surrounding the diseased organ, the coil being energized by a pure DC voltage having a rectangular wave form pulsing at the rate of 1–30 CPS.

7 Claims, 3 Drawing Sheets

TREATMENT OF ACUTE DISEASES AS CAUSED BY THE SPORTS-TYPE INJURIES OF THE MUSCULOSKELETAL SYSTEM EXCLUDING FRACTURES WITH MAGNETIC FIELD THERAPY

This application is a continuation-in-part of application Ser. No. 519,410 filed May 4, 1990, now U.S. Pat. No. 5,131,904.

BACKGROUND OF THE INVENTION

1. Field of the Invention

This invention relates to the treatment of acute diseases or conditions, as from a sports injury, of the musculoskeletal system excluding fractures with magnetic field therapy. More specifically, the diseased organ is treated by being placed inside an annular coil driven by a pulsed DC voltage having a rectangular wave form pulsing at the rate of 1–30 pulse bursts per second producing a low intensity field.

2. Description of Related Art including Information Disclosed under §§1.97 to 1.99

It has been recognized in the prior art that the application of a magnetic field to diseased organs can in some way improve the condition. An example is disclosed in the Kraus patent, U.S. Pat. No. 3,915,151, which discloses the idea of imparting a low frequency AC source to a wound toroid into which an ailing limb is inserted. The imparted voltage creates a changing magnetic field. This treatment is coupled in Kraus with a galvanic action by means of plates disposed on either sides of the limb. A more recent patent, U.S. Pat. No. 4,537,181 to Shaloob et al, discloses treating a patient with a magnetic field created by rotating permanent magnets.

Other patents somewhat of interest to the present invention are U.S. Pat. No. 4,233,965 issued Nov. 18, 1980 and U.S. Pat. No. 4,758,429 issued Jul. 19, 1988.

SUMMARY OF THE INVENTION

Under the present invention the target organ is subjected to an electromagnetic field driven by a pure DC voltage having an abruptly rising and abruptly deteriorating wave form at the rate of 1–30 cycles per second. The field at the target organ is of low intensity, preferably under 20 gauss, and the field lines are oriented, where the target organ is on an appendage, such that the flux lines travel toward the distal end of the appendage.

The effect of the treatment under the present invention is dramatic as will be demonstrated in examples hereunder. The exact mechanism by which the treatment derives its efficacy is not known but one explanation may be found in the uni-directonal elongated (extended) prolongation and abruptly shortened repolarization theory:

Directing a specific time frequency and wave form, of low amplitude magnetic field (flux) into and onto a target area of living tissue/organ in an almost axial arrangement for an extended specified length of time, allows (causes) the electron (ionic) flow to remain in either a plus or minus state. This action does stimulate the electrical potential. Thus a regeneration (repair) process is initiated by (during) which the cells (tissue/organs) are able to and will (better) more fully perform their intended genetic function(s).

The cells (tissue/organs) may therefore carry out their functions in a more appropriate fashion and healthy physiological intended manner. The healing process, once stimulated, is hence-forth maintained by nature of the permanently enhanced positive electron balance and healthy metabolic status.

In amplification of the above theory, I have concluded from a careful review of recent data concerning the intrinsic magnetic field strength of living individuals that all human beings possess measurable amounts of a magnetic field (MF). The data further indicates that most healthy people have a MF which ranges from X to Y gauss. Some human beings have extremely low MF levels: other human beings have extremely high MF levels, i.e. 4 to 5 times (X+Y/2). Based on a correlation between healthy and morbid human beings, I postulate that further investigation should be initiated which might suggest that altered magnetic properties may represent the state of disease, that is, derangement of MF may correlate with disease.

The following specification represents a new approach based on the above theory.

BRIEF DESCRIPTION OF THE DRAWINGS

Other features and objects of the invention will be clear from the following specification including the drawings, all of which disclose a non-limiting form of the invention. In the drawings.

DESCRIPTION OF THE PREFERRED EMBODIMENT

Figure 2:
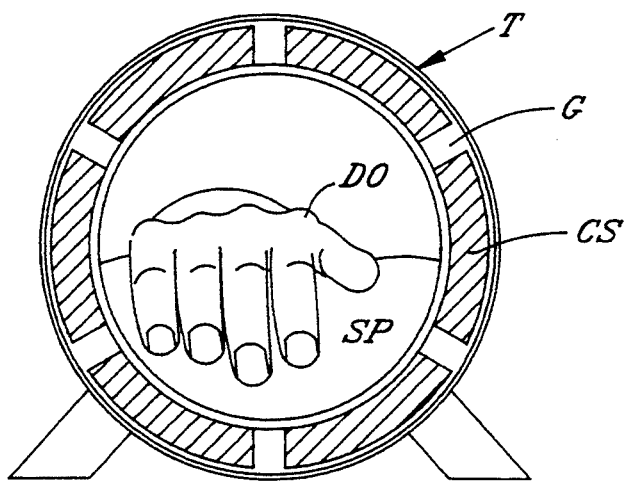
FIG. 2 is a front end view with front of cover removed and showing the coil segments inside the toroid.

Referring to the drawings, the invention involves the creation of an electromagnetic field F. This field is created by energizing a winding in a toroid T such that the field forms a three-dimensional donut in and about the toroid. The toroid T within its case contains s number of coil segments CS spaced by air gaps G as shown in FIG. 2. It is an important characteristic of the invention that the field not be greater than 20 gauss in the area of the diseased organ DO.

Figure 3:
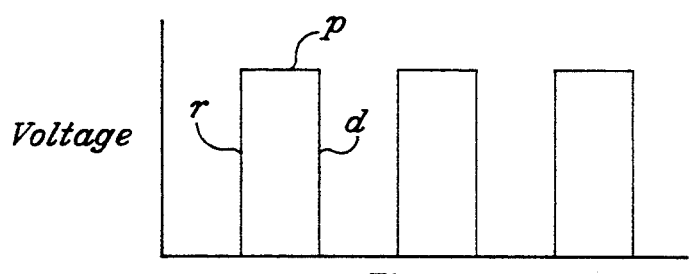
FIG. 3 is a graph showing the voltage flow vs. time as imparted to the toroid air coil to induce the magnetic field under the invention.

After much study, it has been found that it is important that voltage be supplied to the toroid winding in a pattern demonstrated in FIG. 3. The voltage supplied must repeatedly build up steeply, hold, and then deteriorate steeply and so that there are thus created a series of spaced working plateaus p of pure DC current. It is preferred, therefore, that in the duty cycle the wave form of the pure DC voltage involved be virtually of rectangular shape with the abruptly rising r and abruptly falling d sides of the wave form comprising sides of a rectangle. In between two such duty cycles there is an off cycle.

As an additional characteristic, further study has indicated that it is important that the movement of the field along the diseased limb, for instance, be toward its distal end. Thus, for instance, when treating a patient's hand as shown, or knee, as the diseased organ, the magnetic lines of the field F in the area of the organ should move toward the end of the appendage remote from the torso. This is achieved by supplying voltage of proper polarity to the coil leads of the toroid T.

As shown in FIG. 2, the target diseased organ DO is supported to be in position eccentric to the central flux portion of the magnetic field within the toroid. This can be accomplished by a shapeable fiber support pillow SP of cotton or the like which need not completely surround the organ, but should assist its proper positioning. Inside the toroid housing, as stated, are a series of circularly arranged arcuate segments, of wound coil CS. With respect to the size of the toroid, it is important that the distance between the organ and the windings be no greater than about six inches (6").

It has further been found, as a result of much experimentation, that the length of time intervals between the treatment periods and the length of the treatment periods themselves is important. Preferably the length of periods should be no greater than one-half hour and the frequency should be every 24 to 48 hours through the treatment period.

DESCRIPTION OF APPARATUS FOR TREATING ORGANS IN THE TORSO

The invention also has application, aside from treatment of the limbs, to diseased organs on the main part of the body, i.e., the torso. Equipment which has been used for such torso treatment is shown in the drawings, FIGS. 4 through 7.

Figure 4:
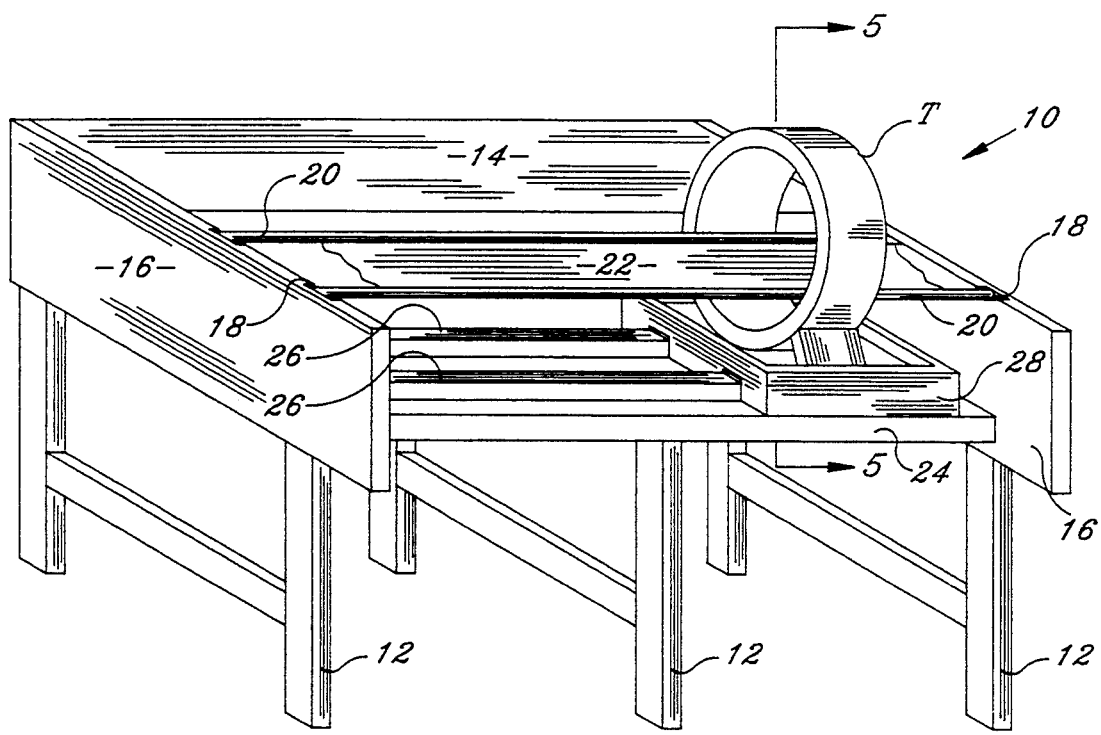
FIG. 4 is a perspective view of a table embodying an apparatus of the invention.
Figure 5:
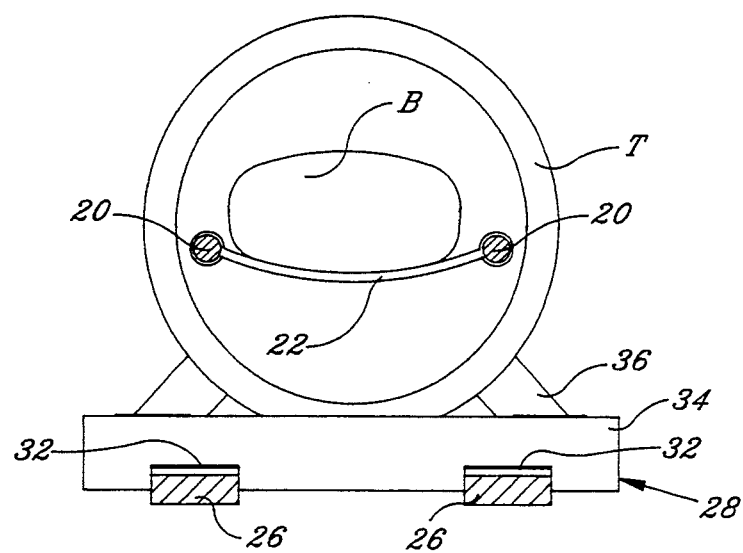
FIG. 5 is an enlarged front end view of the carriage showing the tracks in section.
Figure 6:
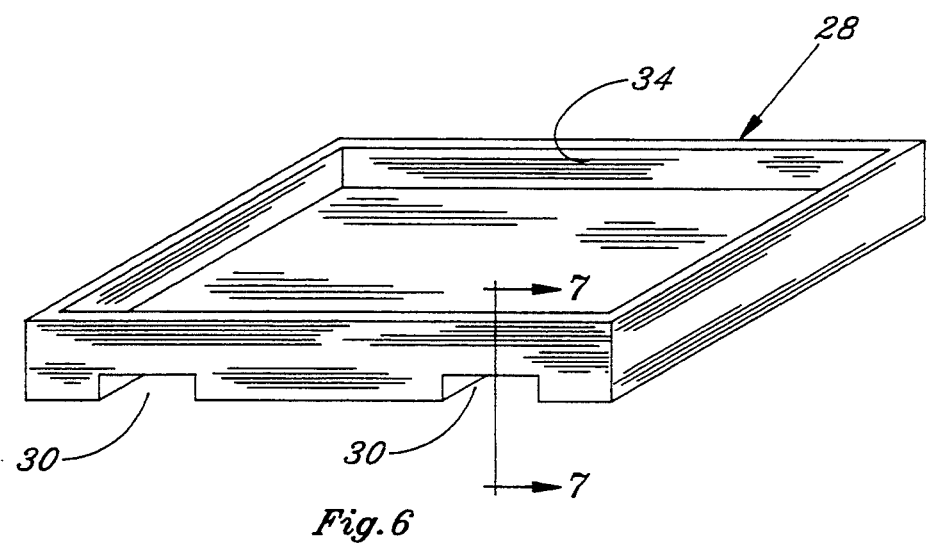
FIG. 6 is an enlarged perspective view of the carriage for supporting the toroid.
Figure 7:
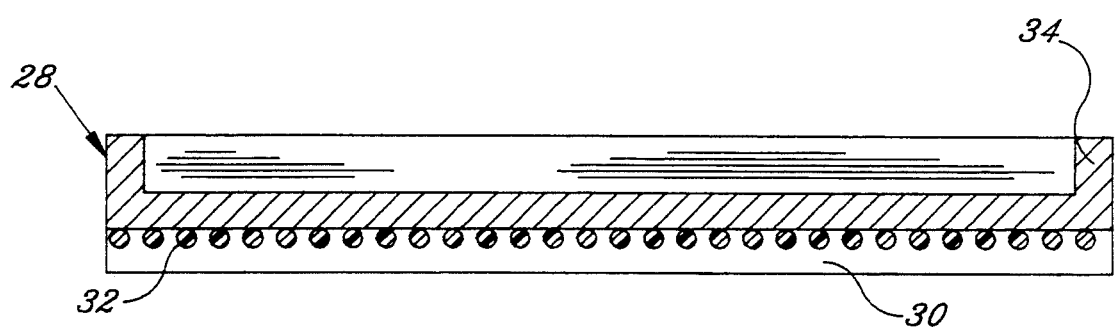
FIG. 7 is a sectional view taken on the line 7—7 of FIG. 6.

FIG. 4 shows an apparatus useful in applying a magnetic field to the main part of the human body, i.e. the torso. It is generally designated 10 and is an all wood table comprising a plurality of support legs 12, a horizontal transitional surface 14 on which the patient may sit and then recline and prepare himself. The support surface 14 is preferably supported on a pair of end boards 16 which are supported by the legs and are notched as at 18 to support rails 20 which has between them a fabric support web 22.

Extending between the side board 16 and horizontally disposed at a level below the surface 14 is a coil support bed 24. Supported on the bed 24 are a pair of spaced parallel tracks 26 which may be in the form of boards having a rectangular cross section. A coil support carriage 28 is provided with a pair of side-by-side upward recesses 30 which fit slideably over the tracks 26.

Figure 1:
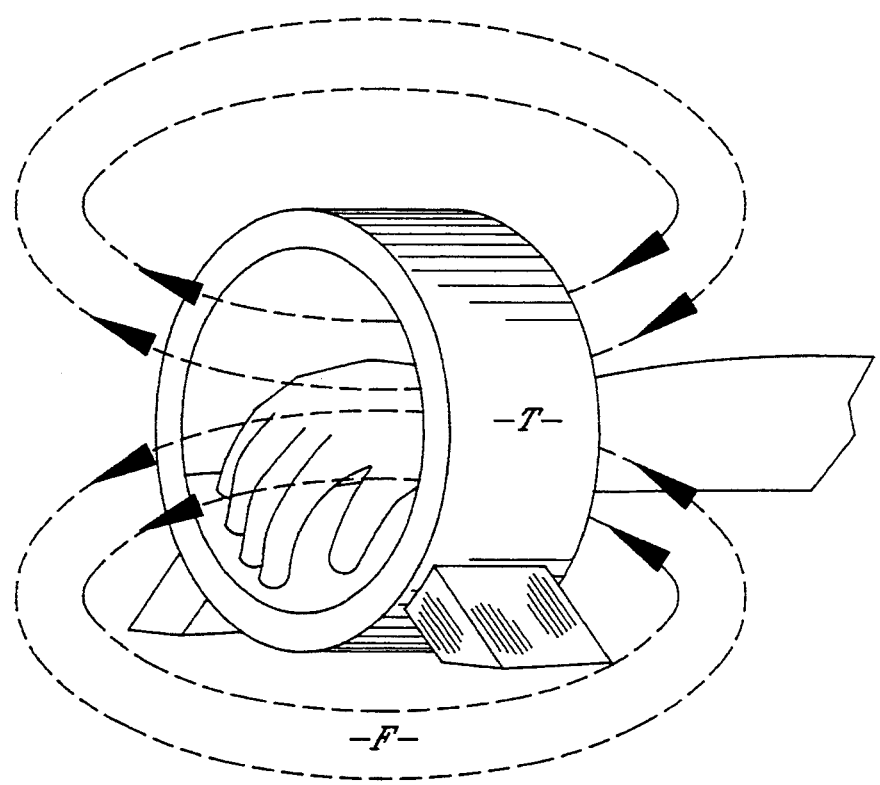
FIG. 1 is a simplified perspective view of a wound toroid energized to develop an electromagnetic field as indicated by flux lines, shown treating a diseased hand.

Anti-friction means, such as plastic rollers 32, are mounted adjacent the upper wall of the recess 30 so that the carriage may easily move along the tracks. Preferably the upper sides of the carriage are formed with a circumferential lip 34. The toroid T, similar to that disclosed in FIGS. 1 and 2, is equipped with downward flaring legs 36 which are received onto the carriage 28 to support the toroid.

In use, the patient reclines on the surface 14 and then, with the carriage 28 at one end of the tracks 26, the patient rolls onto the fabric support web 22 so that his body B is supported thereby. The carriage then moves along the tracks 26 until the toroid T, encompassing his body, is aligned with the diseased organ. The toroid is then energized for treatment as described above.

I have found that for treatment of the hand a toroid having an opening of 5½ is preferable, an opening of 11" may be useful in treatment of the knee and for a treatment of the entire body, as in FIGS. 4 through 7, an opening of 22" is suitable for most patients.

EXAMPLES

The following examples of treatment show results after indicated procedures, all within the scope of the invention as described above.

Example 1

Patient #1 had a recent (acute) injury to the left shoulder while pitching for his company's softball team. This patient is a regular member of the company team. The symptoms in the left shoulder were described as "pain with limitation of movement" which persisted for several weeks. Normal treatment included pain medication (analgesics) and ice packing which did not provide relief. On examination, the patient was found to have a classic rotator cuff injury. Following 18 magnetic therapy (MT) treatments as described herein, complete return to an asymptomatic state with no further pain and a full range of motion were effected, with no reported recurrence of symptoms.

Examples 2 and 3

Patients #2 and #3 had recent onset of right and left elbow pain at the lateral epicondyle (tennis-elbow) which was acute in nature, having been sustained within the past two months. Both patients being professionals, they under took all medical modalities that were available, without relief. On examination, both patients had moderate to severe point tenderness with increased pain upon forced wrist extension. One patient could not rest his elbow on a cushion without noting severe pain. Both patients had extreme limitation of range of motion. Both patients responded significantly after 18 magnetic therapy treatments, as described herein. They have resumed normal working and sports activities without recurrence of symptoms to date.

Example 4

Patient #4 is a fireman who sustained an acute muscle injury to his left upper arm (tricep muscle) approximately one month before presentation. The injury being job related, this patient was examined and evaluated by an orthopedic surgeon, who recommended that rest, followed by a long period of exercise retraining (rehabilitation) would be the best course of treatment. The patient was physician-referred to magnetic therapy for 18 MT treatments. Thereafter, the patient had no further pain nor limitation of motion of the left arm. One month after the final MT treatment he was able to fully resume the demanding physical activities of a fireman.

Example 5

Patient #5 is a 45 year old former professional ballerina who now actively teaches classic dance (ballet) on a daily basis. Having suffered various injuries over the years, she now presented with a recent onset of acute pain and loss of range of motion of her left hip. This acute injury prevented her from continuing her classical dance teaching activities. After a course of 18 MT treatments, the patient's symptoms improved significantly and she was able to fully resume her classical dance teaching activities on a daily basis. The patient was then able to actively participate in a stage performance. This patient has maintained an active role in the dance company since the completion of treatment.

Example 6

Patient 6 is a Black Belt in Karate who suffered an acute injury of the lower back two months prior in training. The patient had severe pain to the lower back and was barely able to walk. He was awakened every night by pain. Upon examination, the patient had extreme pain and difficulty with any and all movements of the lower back, including walking, sitting and bending. After 18 MT treatments the patient had a full recovery of his range of motion with no pain whatsoever. Having had an excellent response without assuming the risks of medicine or surgery, the patient resumed his Karate activities four weeks after completion of his course of treatment, and has remained pain free and able to compete in karate exhibitions to date.

As stated, the invention is susceptible of various changes and is not limited as described in the examples above. The invention may be, therefore, defined as having the scope of the following claim language or reasonable equivalents thereof.

What is claimed is:

1. A treatment of acute disease of a body organ of the musculoskeletal system as caused by a sports-type injury excluding fractures with magnetic field therapy, the process performed in the absence of any electrical field and including the step of subjecting the diseased body organ to an electromagnetic field of under 20 Gauss and generated by an annular coil inside which the body organ is placed, the coil being driven by a pulsed DC voltage having a rectangular wave form consisting of an abruptly rising and abruptly deteriorating current pulsing at the rate of 1–30 pulse bursts per second.

2. A treatment process as claimed in claim 1 wherein said organ is an appendage and wherein the electromagnetic field and the flux lines thereof are oriented so that the lines travel along said appendage in a direction toward the distal end of the appendage, remote from the torso.

3. A treatment process as claimed in claim 1 wherein the electromagnetic field is about 12.5 gauss.

4. A treatment process as claimed in claim 1 wherein the organ is no further away from the source of the field than six inches.

5. A treatment process as claimed in claim 1 wherein the treatment is performed for about 30 minutes every 24–48 hours during the course of treatment.

6. A treatment process as claimed in claim 1 wherein the injury is an acute tendinitis.

7. A treatment process as claimed in claim 1 wherein the injury is acute bursitis.

* * * * *

UNITED STATES PATENT AND TRADEMARK OFFICE
CERTIFICATE OF CORRECTION

PATENT NO. : 5,387,176
DATED : February 7, 1995
INVENTOR(S) : Richard Markoll

It is certified that error appears in the above-indentified patent and that said Letters Patent is hereby corrected as shown below:

On the title page, item [54] and column 1, lines 2-5, the title should read as follows:--TREATMENT OF ACUTE DISEASES AS CAUSED BY SPORTS-TYPE INJURIES OF THE MUSCULOSKELETAL SYSTEM EXCLUDING FRACTURES WITH MAGNETIC FIELD THERAPY--.

Signed and Sealed this

Twenty-first Day of March, 1995

Attest:

BRUCE LEHMAN

Attesting Officer *Commissioner of Patents and Trademarks*